(12) United States Patent
Putzien et al.

(10) Patent No.: US 9,643,948 B2
(45) Date of Patent: May 9, 2017

(54) 2-OXO-1,3-DIOXOLANE-4-ACYL HALIDES, THEIR PREPARATION AND USE

(71) Applicant: Construction Research & Technology, GmbH, Trostberg (DE)

(72) Inventors: Sophie Putzien, Ampfing (DE); Maximilian Köhler, Trostberg (DE); Heimo Wölfle, Traunstein (DE); Burkhard Walther, Taching am See (DE)

(73) Assignee: Construction Research & Technology GmbH, Trostberg (DE)

( * ) Notice: Subject to any disclaimer, the term of this patent is extended or adjusted under 35 U.S.C. 154(b) by 0 days.

(21) Appl. No.: 14/899,638

(22) PCT Filed: May 15, 2014

(86) PCT No.: PCT/EP2014/059973
§ 371 (c)(1),
(2) Date: Dec. 18, 2015

(87) PCT Pub. No.: WO2014/206636
PCT Pub. Date: Dec. 31, 2014

(65) Prior Publication Data
US 2016/0145232 A1    May 26, 2016

(30) Foreign Application Priority Data

Jun. 26, 2013 (EP) ..................................... 13173801

(51) Int. Cl.
*C07D 317/36* (2006.01)
*C07B 41/08* (2006.01)

(52) U.S. Cl.
CPC ............ *C07D 317/36* (2013.01); *C07B 41/08* (2013.01)

(58) Field of Classification Search
CPC ................................................... C07D 317/36
USPC ........................................................ 549/229
See application file for complete search history.

(56) References Cited

U.S. PATENT DOCUMENTS

| | | |
|---|---|---|
| 7,968,572 B2 | 6/2011 | Nakai et al. |
| 8,044,194 B2 | 10/2011 | Dubois et al. |
| 2010/0063104 A1 | 3/2010 | Nakai et al. |
| 2010/0317838 A1 | 12/2010 | Dubois et al. |
| 2011/0313177 A1 | 12/2011 | Mecfel-Marczewski et al. |
| 2014/0228583 A1 | 8/2014 | Mecfel-Marczewski et al. |
| 2015/0051365 A1 | 2/2015 | Woelfle et al. |
| 2015/0353521 A1 | 12/2015 | Wölfle et al. |

FOREIGN PATENT DOCUMENTS

| | | |
|---|---|---|
| EP | 0 001 088 A1 | 3/1979 |
| EP | 1 932 840 A1 | 6/2008 |
| EP | 1 941 948 A1 | 7/2008 |
| EP | 2 397 474 A1 | 12/2011 |

(Continued)

OTHER PUBLICATIONS

Morrison and Boyd, 3rd ed. (1974), pp. 601-603.*

(Continued)

*Primary Examiner* — Taofiq A Solola
(74) *Attorney, Agent, or Firm* — Curatolo Sidoti Co., LPA; Joseph G. Curatolo; Salvatore A. Sidoti

(57) ABSTRACT

The present invention suggests 2-oxo-1,3-dioxolane-4-acyl halides of formula (I),

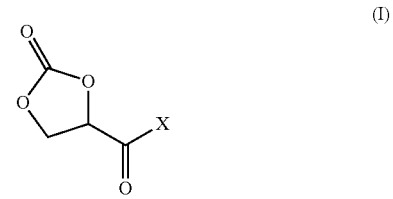

wherein X is selected from F, Cl, Br, I and mixtures thereof, preferably Cl, processes for the preparation of said 2-oxo-1,3-dioxolane-4-acyl halides, the use of said 2-oxo-1,3-dioxolane-4-acyl halides for the preparation of 2-oxo-1,3-dioxolane-4-carboxylic esters of formula (II),

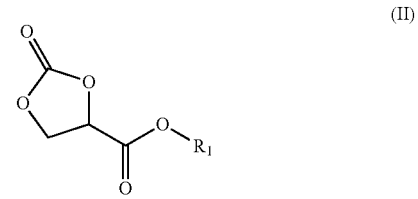

the use of said 2-oxo-1,3-dioxolane-4-acyl halides for the preparation of 2-oxo-1,3-dioxolane-4-carboxamides of formula (III),

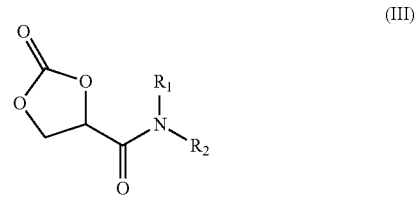

and also the use of said 2-oxo-1,3-dioxolane-4-acyl halides as agents for the blocking of amines.

11 Claims, No Drawings

(56) References Cited

FOREIGN PATENT DOCUMENTS

| JP | 7-285960 A | 10/1995 |
| JP | 2006003433 A | 1/2008 |
| WO | WO 2004/003001 A1 | 1/2004 |
| WO | WO 2007/040208 A1 | 4/2007 |
| WO | WO 2011/157551 A1 | 12/2011 |

OTHER PUBLICATIONS

PCT/EP2014/059973—International Search Report, mailed Jul. 7, 2014.
PCT/EP2014/059973—International Written Opinion, mailed Jul. 7, 2014.
PCT/EP2014/059973—International Preliminary Report on Patentability, issued Dec. 29, 2015.
Tomita, et al., "Model Reaction for the Synthesis of Polyhydroxyurethanes from Cyclic Carbonates with Amines: Substituent Effect on the Reactivity and Selectivity of Ring-Opening Direction in the Reaction of Five-Membered Cyclic Carbonates with Amine", Journal of Polymer Science, 2001, vol. 39, pp. 3678-3685, John Wiley & Sons Inc.
Lewis, et al., "Synthesis of L-660,631 Methyl Ester and Related Compounds", Tetrahedron Letters, Jan. 1, 1988, vol. 29, No. 19, pp. 2279-2282, Pergamon Press PLC, Great Britain.
Diakoumakos, Constantino, et al., "Non-Isocyanate-Based Polyurethanes Derived upon the Reaction of Amines with Cyclocarbonate Resins", Macromol. Symp., 2004, vol. 216, pp. 37-46.
Petit, Y., et al., "Ethyl Glycidate From (S)-Serine: Ethyl (R)-(+)-2,3-Epoxypropanoate", Organic Synthesis Collection, 2004, vol. 10, p. 401; Organic Syntheses, 1998, vol. 75, p. 37.
Stevenson, Christian P., et al., "Preparation of (S)-Methyl Glycidate VIA Hydrolytic Kinetic Resolution", Organic Syntheses, 2006, vol. 83, pp. 162-169; Organic Syntheses Collection, 2009, vol. 11, pp. 157-163.
Lima, et al., "Bioisoterism: A Useful Strategy for Molecular Modification and Drug Design", Current Medicinal Chemistry, 2005, vol. 12, pp. 23-49, Bentham Science Publishers, Ltd.

* cited by examiner

2-OXO-1,3-DIOXOLANE-4-ACYL HALIDES, THEIR PREPARATION AND USE

CROSS REFERENCE TO RELATED APPLICATIONS

This application is a national stage application of International Application No. PCT/EP2014/059973, filed 15 May 2014, which claims priority from European Patent Application No. 13173801.5, filed 26 Jun. 2013, which applications are incorporated herein by reference.

The present invention relates to 2-oxo-1,3-dioxolane-4-acyl halides of formula (I),

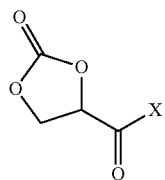

(I)

wherein X is selected from F, Cl, Br, I and mixtures thereof, to processes for the preparation of said 2-oxo-1,3-dioxolane-4-acyl halides, to the use of said 2-oxo-1,3-dioxolane-4-acyl halides for the preparation of 2-oxo-1,3-dioxolane-4-carboxylic esters of formula (II)

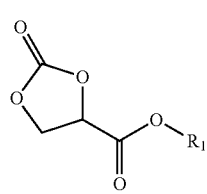

(II)

wherein $R_1$ is selected from straight-chain, branched or cyclic $C_{1-12}$-alkyl groups, $C_{6-10}$-aryl groups, $C_{6-12}$-aralkyl groups and $C_{6-12}$-alkaryl groups, to the use of said 2-oxo-1,3-dioxolane-4-acyl halides for the preparation of 2-oxo-1,3-dioxolane-4-carboxamides of formula (III),

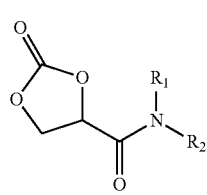

(III)

wherein $R_1$ and $R_2$, in each case independently of one another, are selected from H, straight-chain, branched or cyclic $C_{1-12}$-alkyl groups, $C_{6-10}$-aryl groups, $C_{6-12}$-aralkyl groups and $C_{6-12}$-alkaryl groups or, together with the N atom to which they are bonded, form a 5- to 8-membered ring, and also to the use of said 2-oxo-1,3-dioxolane-4-acyl halides as agents for the blocking of amines.

Structurally similar compounds are already known in the prior art. For example, WO 2004/003001 A1 describes compounds of the general formula (IV)

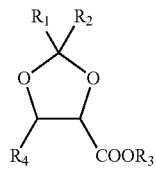

(IV)

where $R_1$ and $R_2$ may be radicals independent of one another, $R_1+R_2=O$ or $CR_1+R_2$ may be a 3-6-membered cycloalkyl group. $R_4$ may be hydrogen, straight-chain or branched $C_{1-8}$-alkyl, $C_{5-12}$-cycloalkyl or $C_{6-15}$-aryl. $R_3$ may be straight-chain or branched $C_{1-8}$-alkyl or $C_{6-15}$-aryl. In general, WO 2004/003001 A1 describes the enzymatic racemate separation of the enantiomers of type (VI) but without indicating a synthesis for these compounds.

EP 1941946 A1 describes the use of a carbonitride catalyst inter alia for the preparation of certain disubstituted organic carbonates. These may also be compounds of the general formula (V),

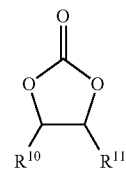

(V)

where $R^{10}$ and $R^{11}$, independently of one another, are selected optional substituents. Possible meanings of the substituents are alkyl, aryl, herteroaryl and ester groups $CO_2A$, where A may in turn be alkyl or aryl, e.g. straight-chain or branched $C_{1-6}$-alkyl, preferably $C_{1-3}$-alkyl and particularly preferably methyl or ethyl. However, no syntheses for 2-oxo-1,3-dioxolane systems are stated.

JP 2006-003433 A discloses a sealing composition for liquid crystal display elements which comprises a compound of the general formula (VI),

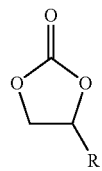

(VI)

where R is H, a hydroxyl group, a cyano group, a carboxylic acid group, an optionally substituted aromatic ring, a straight-chain, branched or cyclic alkyl group, an acyl group or an ester group. The 2-oxo-1,3-dioxolane-4-carboxylic acid (R=COOH) is also mentioned.

EP 0001088 A1 describes inter alia 2-oxo-1,3-dioxolanes of the general formula (VII), where R can be H or $CH_3$.

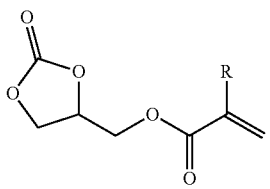

(VII)

EP 2397474 A1 describes 2-oxo-1,3-dioxolane-4-carboxylic esters of formula (VIII)

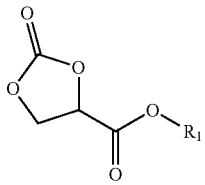

(VIII)

in which $R_1$ may preferably be Me or Et or an n-valent radical which may be substituted with a maximum of n−1 further 2-oxo-1,3-dioxolane-4-carboxyl groups, a process for their preparation by means of carboxylation of the corresponding epoxides, a process for their transesterification, and also their use for the preparation of hydroxyurethanes and as end groups for the blocking of amines.

US 2010/0317838 A1 describes compounds of formula (IX)

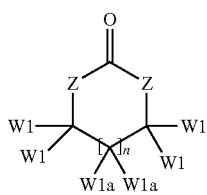

(IX)

in which Z can be O and n can be 0, and at least one of the radicals W1 or W1a comprises a protected glycoside, and each of the radicals W1 and W1a, independently of one another, may inter alia also be an amide group.

Polyurethanes based on polyisocyanates belong to the prior art. These are used for example as adhesives, sealants, casting compositions, as corrosion protection and for coatings. The high resistance to acids, alkalis and chemicals of the cured compositions obtained in this way are advantageous. However, monomeric low molecular weight (poly) isocyanate compounds are toxicologically unacceptable, especially if they are readily volatile or migrate.

Polyurethane systems can also be obtained starting from cyclic carbonate compounds, which are toxicologically acceptable. Thus, for instance, glycerol carbonate (4-(hydroxymethyl)-2-oxo-1,3-dioxolane) is regularly used in cosmetics, i.e. it is non-toxic.

Cyclic carbonate compounds react with amines with ring opening inter alia to give hydroxyurethanes (cf. formula scheme below):

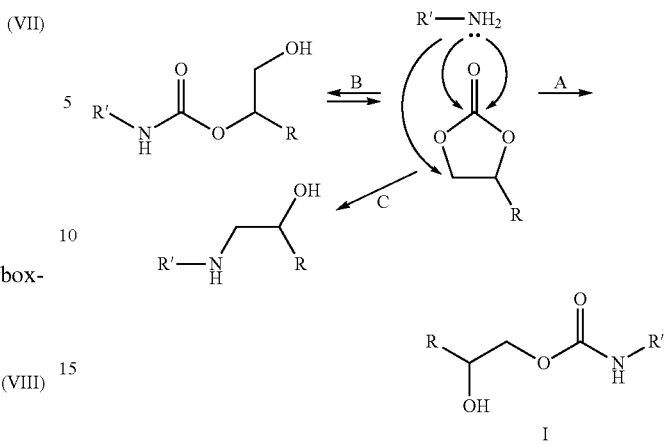

I

Disadvantages of the systems based on glycerol carbonate are the low regioselectivity, which leads to reaction pathways A, B and C, the comparatively low reactivity of the systems at room temperature, and the fact that catalysts which increase the rate of the ring opening obviously also promote the back-reaction, which can lead to a partial decomposition of the products already formed.

In the aforementioned EP 2397474 A1, these problems have been partially solved by using an ester group instead of an ether group in R. This electron-withdrawing group led to a considerable increase in the rate of the reaction and to a preference for reaction pathway A. In the case of the secondary hydroxyurethanes [I] formed, no back-reaction was observed. However, the production of binders which comprise two or more 2-oxo-1,3-dioxolane-4-carboxyl groups in the molecule is difficult since this takes place via a transesterification, during which the cyclocarbonate ring can also be attacked.

The aforementioned US 2010/0317838 A1 gives the impression that this ring opening reaction is independent of the nature of R (cf. claim 17 of US 2010/0317838 A1 which is directed to the ring opening of compounds of claim 1 which may contain ester groups or amide groups alike). However, this impression is quite misleading.

Firstly, studies have been carried out (cf. H. Tomita, F. Sanda, T. Endo, Journal of Polymer Science: Part A: Polymer Chemistry, Vol. 39, 3678-3685 (2001)) according to which the reactivity of the 2-oxo-1,3-dioxolanes, which are substituted in 4-position with the group R, with amines increases in the order: R=Me<R=H<R=Ph<R=$CH_2$OPh<<R=$CF_3$.

Secondly, in the case of the products of the aforementioned EP 2397474 A1 where the polymeric main chain is attached through ester bonds, i.e. R in the formula scheme below means the polymeric main chain, the ring opening (hardening) reaction is accompanied by a certain amount of aminolysis of the ester bond leading to the detachment of the main chain in the form of an unreactive alcohol.

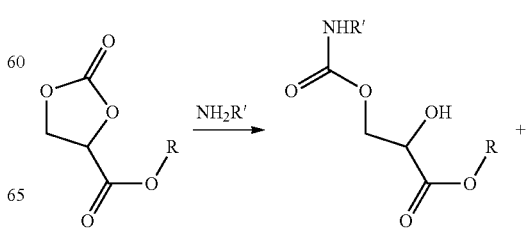

-continued

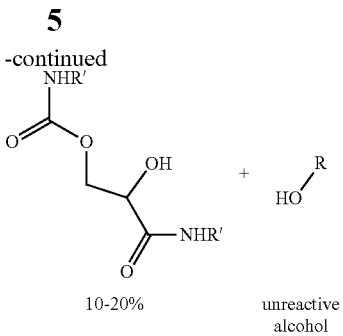

10-20%     unreactive alcohol

In the case of the amides as disclosed in PCT/EP2012/072589 of 14.11.212 with priority of 22.12.2011, aminolysis is per se not possible. If any transamination occurred, the formed amine would be capable of acting as a reactive hardener to attack further cyclic carbonate groups. Cross-linking and hardening of the products are thus much higher. This follows from the formula scheme below.

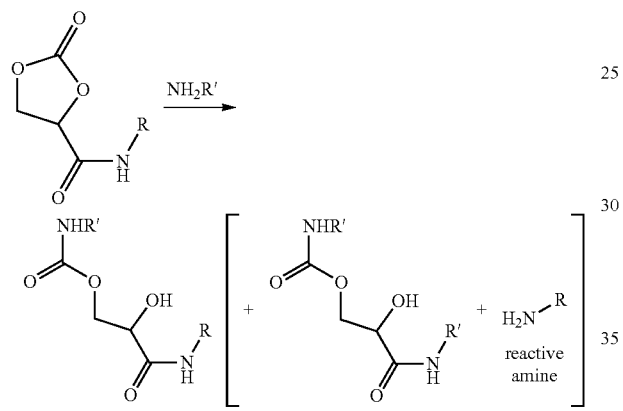

This is a clear advantage of the -4-carboxamides over the -4-carboxylic esters. However, the -4-carboxamide derivatives in the aforementioned PCT/EP 2012/072589 were synthesized e.g. by using toxic isocyanates (cf. Example 9 thereof):

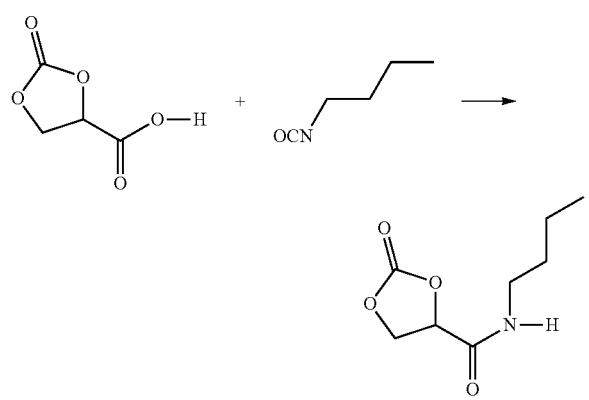

It was the object of the present invention to essentially avoid at least some of the disadvantages of the prior art described above. In general terms, the aim was to provide an alternative 2-oxo-1,3-dioxolane system with an electron-withdrawing group. In particular, the aim was to provide a 2-oxo-1,3-dioxolane system which is toxicologically acceptable, readily accessible and possesses higher reactivity towards alcohols and amines so that the aforementioned -4-carboxamides and -4-carboxylic esters could be easily synthesized.

This object has been achieved with the features of the independent claims. The dependent claims relate to preferred embodiments.

The present invention provides a 2-oxo-1,3-dioxolane-4-acyl halide of formula (I),

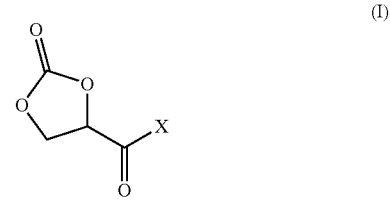

(I)

wherein X is selected from F, Cl, Br, I and mixtures thereof. In a preferred embodiment of the present invention X is Cl. (2-Oxo-1,3-dioxolane-4-acyl halides may also be called 2-oxo-1,3-dioxolane-4-carbonyl halides.)

The present invention also provides a process for the preparation of a 2-oxo-1,3-dioxolane-4-acyl halide as defined hereinabove, wherein 2-oxo-1,3-dioxolane-4-carboxylic acid of formula (X)

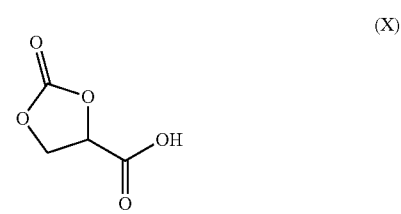

(X)

is reacted with an halogenation agent. In a preferred embodiment the halogenation agent is $SOCl_2$.

The said halogenation reaction is preferably carried out without a solvent at an elevated temperature. In particular, the halogenation is preferably carried out at about 60° C. in the presence of dimethylformamide as a catalyst.

The key intermediate in the above halogenation reaction is 2-oxo-1,3-dioxolane-4-carboxylic acid, the synthesis whereof being described in the aforementioned PCT/EP2012/072589. According to one embodiment, 2-oxo-1,3-dioxolane-4-carboxylic acid can be prepared by hydrolysing a 2-oxo-1,3-dioxolane-4-carboxylic acid ester of formula (II-$R_1$=Me) in an acidic medium, preferably in aqueous acetic acid. Moreover, according to another embodiment, 2-oxo-1,3-dioxolane-4-carboxylic acid can be prepared by oxi-dizing glycerol carbonate (4-(hydroxymethyl)-2-oxo-1,3-dioxolane) by means of N-oxide-mediated oxidation (see Reference Examples 1 and 2.)

Moreover, the present invention also provides for the use of a 2-oxo-1,3-dioxolane-4-acyl halide of the invention for the preparation of a 2-oxo-1,3-dioxolane-4-carboxylic ester of formula (II),

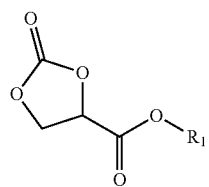

(II)

wherein $R_1$ is selected from straight-chain, branched or cyclic $C_{1-12}$-alkyl groups, $C_{6-10}$-aryl groups, $C_{6-12}$-aralkyl groups and $C_{6-12}$-alkaryl groups. $R_1$ can also be a radical having a valency of 2 to 6 (preferably 2 to 3), which is substituted with 1 to 5 (preferably 1 to 2) further 2-oxo-1,3-dioxolane-4-carboxylic ester groups. It is also possible that $R_1$ is derived from a polyol such as an oligosaccharide or a polysaccharide.

The present invention also provides for the use of a 2-oxo-1,3-dioxolane-4-acyl halide of the invention for the preparation of a 2-oxo-1,3-dioxolane-4-carboxamide of formula (III),

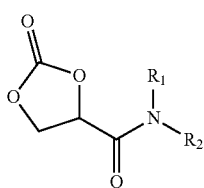

(III)

wherein $R_1$ and $R_2$, in each case independently of one another, are selected from H, straight-chain, branched or cyclic $C_{1-12}$-alkyl groups, $C_{6-10}$-aryl groups, $C_{6-12}$-aralkyl groups and $C_{6-12}$-alkaryl groups or, together with the N atom to which they are bonded, form a 5- to 8-membered ring. $R_2$ can also be a radical having a valency of 2 to 6 (preferably 2 to 3), which is substituted with 1 to 5 (preferably 1 to 2) further 2-oxo-1,3-dioxolane-4-carboxamide groups. It is also possible that $R_1$ is derived from a polyamide.

Finally, the present invention provides for the use of use of a 2-oxo-1,3-dioxolane-4-acyl halide of the invention as an agent for the blocking of amines, i.e. as an end group (so-called "end cap"). This is also of interest with regard to conventional, amine-crosslinked polyurethane systems since an amine excess can lead to discolorations, while an isocyanate excess is toxicologically unacceptable.

The present invention is now illustrated in more detail by reference to the examples hereinbelow.

EXAMPLES

Example 1 (Reference): Acidic Hydrolysis of 4-methoxycarbonyl-2-oxo-1,3-dioxolane

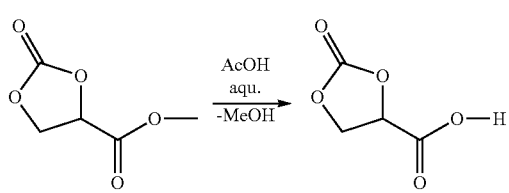

73 g (0.5 mol) of 4-methoxycarbonyl-2-oxo-1,3-dioxolane (EP 2397474 A1) was heated under reflux for 3 hours with 11 g (0.55 mol) of water and 48 g (0.8 mol) of acetic acid. The mixture was then added to cyclohexane, the separated-off oil was carefully freed from all volatile constituents and the residue was ground with methylene chloride until a colourless crystalline precipitate had formed. The precipitate was washed with diethyl ether and dried in vacuo. This gave 2-oxo-1,3-dioxolane-4-carboxylic acid.

m.p.: 119-121° C. $^1$H-NMR (CDCl$_3$/DMSO-d6 (1/0.1 [mol/mol])): 9.486 (broad, s; 1H); 5.012 (dd; 1H); 4.637 (t; 1H); 4.506 (dd; 1H). $^{13}$C-NMR (CDCl$_3$/DMSO-d6 (1/0.1 [mol/mol])): 168.425 (CO acid); 153.348 (CO cyclocarbonate); 72.247 (CH—COOH); 66.988 (CH$_2$CH—COOH). IR (v [cm$^{-1}$]): 2977 bs (OH acid), 2751 bw, 2658 bw, 2621 bw, 2538 bw, 2407 bw, 1785 bm (CO cyclocarbonate), 1793 bs (CO acid), 1546 w, 1481 w, 1431 w, 1399 s, 1345 w, 1325 w, 128 m, 1196 s, 1087 s, 1074 s, 1039 m, 928 w, 832 s, 769 s, 724 m, 699 s, 650 m, 633 s, 525 s.

Example 2 (Reference): N-Oxide-Mediated Oxidation of Glycerol Carbonate

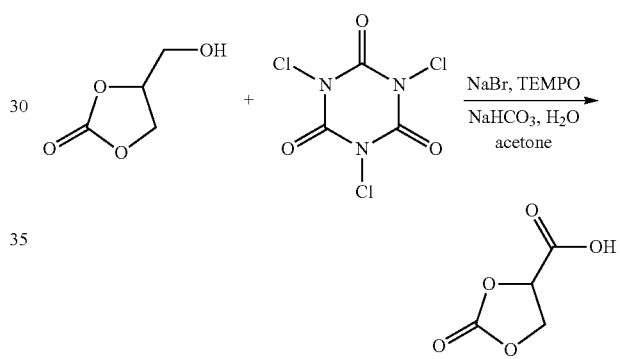

(Procedure analogous to JOC 2003; 68; pages 4999 ff.) 118.1 g (1 mol) of glycerol carbonate, 168 g (2 mol) of sodium hydrogencarbonate, 232 g (1 mol) of trichloroisocyanuric acid, 18 g (1 mol) of water, 1.5 g (0.01 mol) of TEMPO (2,2,6,6-tetramethylpiperidin-1-oxyl) and 5 g (0.05 mol) of NaBr were introduced in 1.5 l of acetone at 0° C. with stirring. The mixture was left to warm to room temperature and stirred for a further 12 hours, after which it was filtered off. The filtrate was concentrated by evaporation. The resulting oil was heated at reflux with chloroform. This gave 2-oxo-1,3-dioxolane-4-carboxylic acid in 97% yield.

Example 3: Synthesis of 2-oxo-1,3-dioxolane-4-acyl chloride

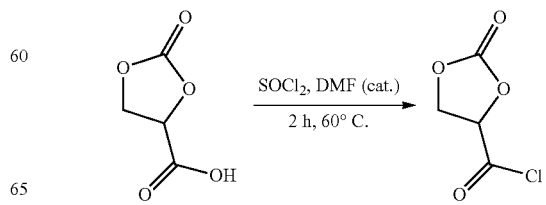

In a dry schlenk tube under an atmosphere of dry N2, 2.5 g (0.019 mol) of 2-oxo-1,3-dioxolane-4-carboxylic acid, 2.5 g (0.021 mol) of freshly distilled thionyl chloride and 0.115 ml of dimethylformamide were heated to 50° C. until the formation of a clear solution. The reaction mixture was heated to 60° C. for 2 h. After DMF and the excess of thionyl chlorid were removed in vacuo, 2-oxo-1,3-dioxolane-4-acyl chloride was obtained as a colorless liquid in quantitative yield.

$^1$H-NMR (400 MHz, DMSO-d6): δ=5.27 (dd, 1H, CH$_2$), 4.71 (t, 1H, CH), 4.52 (dd, 1H, CH$_2$') ppm; $^{13}$C-NMR (100 MHz, DMSO-d6): δ=169.5 (C=O), 154.7 (OC(=O)O), 72.9 (CH), 67.7 (CH$_2$) ppm; IR (v, cm$^{-1}$): 2976 (bw, COOH), 1802 (s, cyclocarbonate), 1668 (w), 1529 (w), 1480 (w), 1385 (m), 1310 (w), 1210 (w), 1147 (s), 1104 (m), 1060 (s), 921 (s), 882 (s), 760 (s), 699 (s), 640 (w), 560 (m), 526 (m); GC-MS (EtAc, RT: 8.73 min): m/z=86.99 [Cyclo-carbonate]$^+$, 62.93 [CClO]$^+$.

Example 4: Reactivity of 2-oxo-1,3-dioxolane acyl chloride

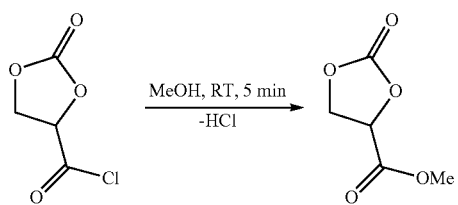 [SMILES: O=C1OCC(C(=O)Cl)O1 ; "-HCl" ; COC(=O)C1COC(=O)O1]

In a dry schlenk tube under an atmosphere of dry N2, to 2.86 g (0.019 mol) of 2-oxo-1,3-dioxolane acyl chloride was carefully added 0.73 g (0.023 mol) of methanol. During the exothermic reaction the evolution of HCl-gas was observed. The reaction was cooled to RT using a cold water bath, the excess of MeOH was removed in vacuo and 2-oxo-1,3-dioxolane carboxylic acid methyl ester was obtained in quantitative yield. The analytical data agree with known data of 2-oxo-1,3-dioxolane carboxylic acid methyl ether.

Example 5: Reactivity of 2-oxo-1,3-dioxolane acyl chloride

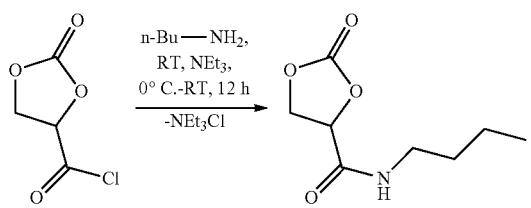

In a dry schlenk flask under an atmosphere of dry N2, 2.86 g (0.019 mol) 2-oxo-1,3-dioxolane carbonyl chloride was diluted with 20 ml abs. THF and cooled to 0-4° C. using an ice bath. In a dropping funnel 0.019 mol n-butylamine and 2.31 g (0.019 mol) triethylamine were mixed and diluted with 10 ml abs. THF. This mixture was carefully added to the acid chloride at 0-4° C. Immediately a white precipitate of Et$_3$NCl formed. The reaction mixture was stirred at 0-4° C. for 1 h and additional 12 h at RT. The precipitate was filtered off and the solvent was removed in vacuo. N-n-butyl-2-oxo-1,3-dioxolane-4-carboxamide was obtained as a brownish oil in 96% yield. Analytic data agree with known data of N-n-butyl-2-oxo-1,3-dioxolane-4-carboxamide prepared from 2-oxo-1,3-dioxolane carboxylic acid and n-butylisocyanate.

Example 6: Reactivity of 2-oxo-1,3-dioxolane acyl chloride

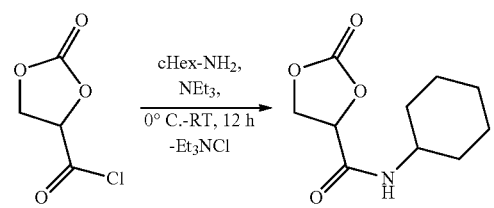 [SMILES: O=C1OCC(C(=O)Cl)O1 ; "0° C.-RT, 12 h-Et3NCl" ; O=C1OCC(C(=O)NC2CCCCC2)O1]

In a dry schlenk flask under an atmosphere of dry N2, 2.86 g (0.019 mol) 2-oxo-1,3-dioxolane-4-carbonyl chloride was diluted with 10 ml abs. THF and cooled to 0-4° C. using an ice bath. In a dropping funnel 1.88 g cyclohexylamine (0.019 mol) and 2.31 g (0.019 mol) triethylamine were mixed and diluted with 20 ml abs. THF. This mixture was carefully added to the acid chloride at 0-4° C. Immediately a white precipitate of Et$_3$NCl formed. The reaction mixture was stirred at 0-4° C. for 1 h and additional 12 h at RT. The precipitate was filtered off and the solvent was removed in vacuo. N-cyclohexyl-2-oxo-1,3-dioxolane-4-carboxamide was obtained as a beige powder in 94% yield. The analytical data agree with known data of N-cyclohexyl-2-oxo-1,3-dioxolane-4-carboxamide prepared from 2-oxo-1,3-dioxolane-4-carboxylic acid and cyclohexyl-isocyanate.

Example 7: Formation and Curing of Multifunctional Binders from 2-oxo-1,3-dioxolane-4-acyl chloride

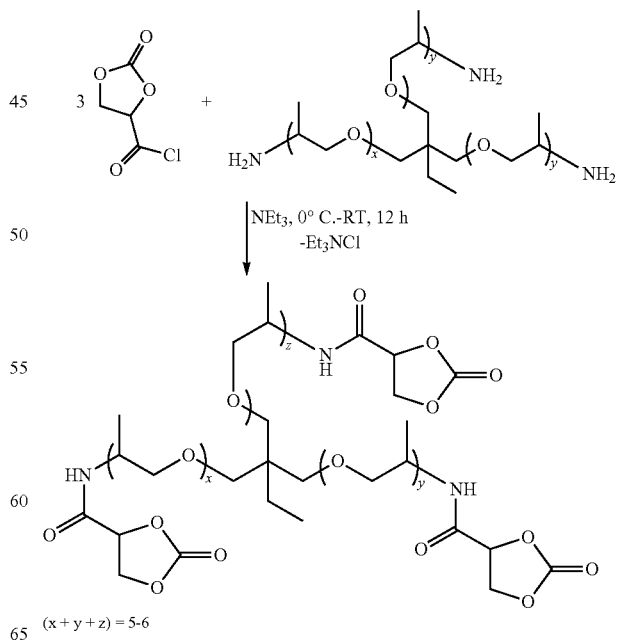

In a dry schlenk flask under an atmosphere of dry N2, 30.10 g (0.2 mol) 2-oxo-1,3-dioxolane carbonyl chloride ("CYCA-chloride") was diluted with 70 ml abs. THF and cooled to 0-4° C. using an ice bath. In a dropping funnel 29.33 g polyetheramine T 403 (BASF SE, 0.2 mol) and 24.29 g (0.24 mol) triethylamine were mixed and diluted with 40 ml abs. THF. This mixture was carefully added to the acid chloride at 0-4° C. Immediately a white precipitate of Et$_3$NCl formed. The reaction mixture was stirred at 0-4° C. for 1 h and additional 12 h at RT. The precipitate was filtered off and the solvent was removed in vacuo. The trifunctional product was obtained as a red-brown oil in almost quantitative yield.

IR (v, cm$^{-1}$): 3311 (bw), 3082 (w), 2972 (w), 2932 (w), 2874 (w), 1811 (s, cyclocarbonate), 1666 (s), 1541 (m), 1456 (m), 1385 (m), 1378 (m), 1255 (w), 1153 (s), 1080 (s), 1060 (s), 922 (w), 840 (w), 768 (m), 730 (w), 661 (w).

The procedure was analogously carried out with Polyetheramine T 5000 (BASF SE) or Jeffamine T 3000 (Huntsman). The properties are summarized in Table 1 hereinbelow:

TABLE 1

|  | Amount [g] | Amount [mol] | Properties |
|---|---|---|---|
| CYCA-chloride | 30.10 | 0.2 | — |
| T 403 | 29.33 | 0.2 | Red-brown viscous liquid, 2.650.000 mPas, Meq = 261 g/mol |
| T 3000 | 200.00 | 0.2 | Red-brown liquid, 10.500 mPas, Meq = 1115 g/mol |
| T 5000 | 333.33 | 0.2 | Red-brow liquid, 6.000 mPas, Meq = 1800 g/mol |
| NEt$_3$ | 24.29 | 0.24 | — |

The resulting products can be cured with different amines to give stable hydroxypoly-urethane films. The results are summarized in Table 2 hereinbelow:

TABLE 2

| Amine | Binder | | |
|---|---|---|---|
|  | T403-CYCA | T3000-CYCA | T5000-CYCA |
| Lupasol ® FG (BASF SE) |  | Cured, tack-free, $\sigma_M$ = 0.99 N/mm$^2$, $\epsilon_M$ = 35% | Cured, tack-free, $\sigma_M$ = 0.44 N/mm$^2$, $\epsilon_M$ = 125% |
| IPDA | Cured, tack-free, brittle | Not completely cured, tacky |  |
| T 403 (Huntsman) | Cured, tack-free, $\sigma_M$ = 0.86 N/mm$^2$, $\epsilon_M$ = 78% | Cured, elastic | Not completely cured, tacky |

Cyclocarbonate-functional binders can also be prepared from 2-oxo-1,3-dioxolane carbonyl chloride using triols (such as Lupranol® 1301 or 2048) instead of triamines.

Example 8: Formation and Curing of Multifunctional Binders from 2-oxo-1,3-dioxolane-4-acyl chloride Cyclocarbonate-functional binders were also prepared from 2-oxo-1,3-dioxolane-4-carbonyl chloride using triols (such as Lupranol 1301 or 2048, BASF SE) instead of triamines:

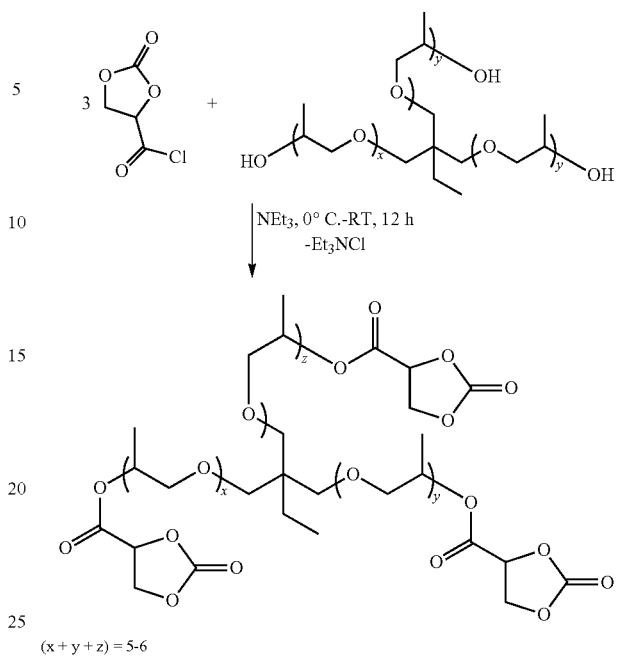

$(x + y + z) = 5-6$

In a dry schlenk flask under an atmosphere of dry N2, 10.00 g (0.07 mol) 2-oxo-1,3-dioxolane-4-acyl chloride were diluted with 200 ml abs. THF and cooled to 0-4° C. using an ice bath. In a dropping funnel 88.18 g Lupranol 2048 (BASF SE, 0.07 mol) and 8.00 g (0.08 mol) triethylamine were mixed and diluted with 50 ml abs. THF. This mixture was carefully added to the acid chloride at 0-4° C. Immediately a white precipitate of Et$_3$NCl formed. The reaction mixture was stirred at 0-4° C. for 1 h and additional 12 h at RT. The precipitate was filtered off and the solvent was removed in vacuo. The trifunctional product was obtained as a red-brown oil in almost quantitative yield. (Lupranol 1301 can be used analogously.)

IR (v, cm$^{-1}$): 2865 (s), 1821 (s, cyclocarbonate), 1752 (m), 1455 (m), 1373 (m), 1349 (m), 1296 (m), 1248 (m), 1090 (vs), 1060 (s), 949 (m), 846 (w), 768 (w).

The resulting products were subsequently cured with different amines to give hydroxy-polyurethane films. The results are summarized in Table 3 hereinbelow:

TABLE 3

| Amine | Binder |
|---|---|
|  | 2048-CYCA (M$_{eq}$ = 255 g/mol) |
| Lupasol FG (BASF SE) | Not completely cured |
| IPDA | Not completely cured |
| T 403 (Huntsman) | Not completely cured |

Due to the lower stability of the ester groups in comparison to the amide groups in the triamine-based products, a poorer curing behavior is observed and less stable films are obtained.

The invention claimed is:
1. 2-Oxo-1,3-dioxolane-4-acyl halide of formula (I),

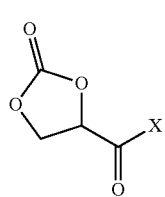
(I)

wherein X is selected from F, Cl, Br, I and mixtures thereof.

2. The 2-Oxo-1,3-dioxolane-4-acyl halide according to claim 1, wherein X is Cl.

3. A process for the preparation of the 2-oxo-1,3-dioxolane-4-acyl halide as defined in claim 1, wherein 2-oxo-1,3-dioxolane-4-carboxylic acid of formula (X)

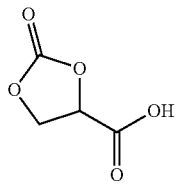
(X)

is reacted with an halogenation agent.

4. The process according to claim 3, wherein the halogenation agent is $SOCl_2$.

5. The process according to claim 4, wherein the reaction is carried out without a solvent at an elevated temperature.

6. The process according to claim 5, wherein the halogenation is carried out at about 60° C. in the presence of dimethylformamide as a catalyst.

7. A process comprising reacting the 2-oxo-1,3-dioxolane-4-acyl halide as defined in claim 1 with an alcohol $R_1$—OH for the preparation of a 2-oxo-1,3-dioxolane-4-carboxylic ester of formula (II),

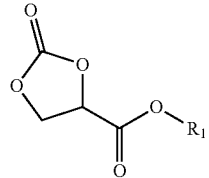
(II)

wherein $R_1$ is selected from straight-chain $C_{1-12}$-alkyl groups, branched or cyclic $C_{3-12}$-alkyl groups, $C_{6-10}$-aryl groups, $C_{6-12}$-aralkyl groups and $C_{6-12}$-alkaryl groups.

8. A process comprising reacting the 2-oxo-1,3-dioxolane-4-acyl halide as defined in claim 1 with a multifunctional polyol comprising $R_1$ for the preparation of a 2-oxo-1,3-dioxolane-4-carboxylic ester of formula (II),

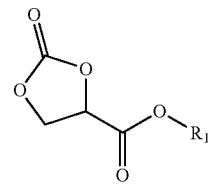
(II)

wherein $R_1$ is a radical having a valency of 2 to 6, which is substituted with 1 to 5 further 2-oxo-1,3-dioxolane-4-carboxylic ester groups.

9. A process comprising reacting the 2-oxo-1,3-dioxolane-4-acyl halide as defined in claim 1 with an amine $NH_2R_1$ for the preparation of a 2-oxo-1,3-dioxolane-4-carboxamide of formula (III),

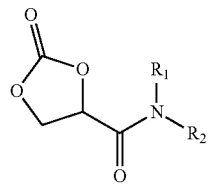
(III)

wherein $R_1$ and $R_2$, in each case independently of one another, are selected from H, straight-chain $C_{1-12}$-alkyl groups, branched or cyclic $C_{3-12}$-alkyl groups, $C_{6-10}$-aryl groups, $C_{6-12}$-aralkyl groups and $C_{6-12}$-alkaryl groups or, together with the N atom to which they are bonded, form a 5- to 8-membered ring.

10. A process comprising reacting the 2-oxo-1,3-dioxolane-4-acyl halide as defined in claim 1 with a multifunctional amine comprising $R_2$ for the preparation of a 2-oxo-1,3-dioxolane-4-carboxamide of formula (III),

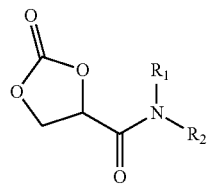
(III)

wherein $R_1$ is selected from H, straight-chain $C_{1-12}$-alkyl groups, branched or cyclic $C_{3-12}$-alkyl groups, $C_{6-10}$-aryl groups, $C_{6-12}$-aralkyl groups, $C_{6-12}$-alkaryl groups, or a polypeptide residue, and $R_2$ is a radical having a valency of 2 to 6, which is substituted with 1 to 5 further 2-oxo-1,3-dioxolane-4-carboxamide groups.

11. A process comprising blocking an amine by reaction with the 2-oxo-1,3-dioxolane-4-acyl halide as defined in claim 1.

* * * * *